(12) United States Patent
Glazer (10) Patent No.: US 9,295,285 B2
(45) Date of Patent: Mar. 29, 2016

(54) SYSTEM AND METHOD TO MANAGE SMOKING

(71) Applicant: Joseph Dennis Glazer, Bronxville, NY (US)

(72) Inventor: Joseph Dennis Glazer, Bronxville, NY (US)

(*) Notice: Subject to any disclaimer, the term of this patent is extended or adjusted under 35 U.S.C. 154(b) by 0 days.

(21) Appl. No.: 14/605,209

(22) Filed: Jan. 26, 2015

(65) Prior Publication Data
US 2015/0208723 A1    Jul. 30, 2015

Related U.S. Application Data

(60) Provisional application No. 61/932,510, filed on Jan. 28, 2014.

(51) Int. Cl.
| | | |
|---|---|---|
| F23Q 3/01 | (2006.01) |
| A24F 47/00 | (2006.01) |
| G09B 19/00 | (2006.01) |
| G06F 19/00 | (2011.01) |
| F23Q 2/32 | (2006.01) |
| F23Q 7/14 | (2006.01) |
| F23Q 2/28 | (2006.01) |
| G06M 3/02 | (2006.01) |

(52) U.S. Cl.
CPC ................ *A24F 47/00* (2013.01); *F23Q 2/325* (2013.01); *F23Q 7/14* (2013.01); *G06F 19/3406* (2013.01); *G06F 19/3481* (2013.01); *G09B 19/00* (2013.01)

(58) Field of Classification Search
CPC ............. F23Q 2/32; F23Q 2/325; F23Q 2/30; F23Q 2/03; F23Q 2/282; F23Q 2/285; F23Q 3/01; G06F 19/3406; G09B 19/00
USPC ......... 431/253, 129, 130, 132, 134, 142, 267, 431/6
IPC   F23Q 3/01,2/32, 2/28, 2/16, 2/34; A24F 47/00; G06M 3/02
See application file for complete search history.

(56) References Cited

U.S. PATENT DOCUMENTS

| | | | | | |
|---|---|---|---|---|---|
| 1,737,964 | A | * | 12/1929 | Esterow | 206/216 |
| 1,774,959 | A | * | 9/1930 | Bolle | 206/216 |
| 1,788,093 | A | * | 1/1931 | Fishel | 431/274 |
| 1,793,515 | A | * | 2/1931 | Segal | 431/276 |
| 1,835,768 | A | * | 12/1931 | Esterow | 206/216 |
| 2,577,679 | A | * | 12/1951 | Fraser | 368/10 |
| 3,544,253 | A | * | 12/1970 | Bloom et al. | 431/253 |
| 4,086,756 | A | * | 5/1978 | Drake | 368/10 |
| 4,092,096 | A | * | 5/1978 | Goto | 431/253 |

(Continued)

FOREIGN PATENT DOCUMENTS

| | | | | | |
|---|---|---|---|---|---|
| FR | 2450419 | A1 | * | 9/1980 | F23Q 2/285 |
| GB | 2140543 | A | * | 11/1984 | F23Q 2/32 |

OTHER PUBLICATIONS

International Search Report and Written Opinion for International Application No. PCT/US2015/013020 mailed May 5, 2015.

*Primary Examiner* — Gregory Huson
*Assistant Examiner* — Daniel E Namay
(74) *Attorney, Agent, or Firm* — Lowenstein Sandler LLP (57) ABSTRACT

A lighter includes a heating element, a data store to store a smoking management plan including one or more rules, and a processor, operatively coupled to the data store and the heating element, to selectively disable activation of the heating element based on the smoking management plan.

23 Claims, 5 Drawing Sheets

(56) References Cited

U.S. PATENT DOCUMENTS

| | | | |
|---|---|---|---|
| 4,102,631 A * | 7/1978 | Goto | 431/253 |
| 4,111,638 A | 9/1978 | Ostberg | |
| 4,311,448 A * | 1/1982 | Strauss | 431/14 |
| 4,368,030 A * | 1/1983 | Benedetti | 431/13 |
| 4,615,681 A * | 10/1986 | Schwarz | A24F 15/005 131/270 |
| 4,853,854 A * | 8/1989 | Behar | G04G 15/006 131/270 |
| 4,947,873 A * | 8/1990 | Wang | 131/329 |
| 5,067,895 A * | 11/1991 | Chuang et al. | 431/253 |
| 5,228,848 A * | 7/1993 | Kim | 431/253 |
| 5,235,157 A | 8/1993 | Blackburn | |
| 7,160,104 B2 * | 1/2007 | Faber | 431/253 |
| 7,976,305 B2 * | 7/2011 | Lin | 431/153 |
| 8,653,942 B2 * | 2/2014 | Gibson et al. | 340/5.82 |
| 8,926,320 B2 * | 1/2015 | Al Gharib | 431/253 |
| 2001/0027794 A1 * | 10/2001 | Brue | A24F 47/00 131/270 |
| 2002/0158812 A1 * | 10/2002 | Pallakoff | H04M 1/0214 345/5 |
| 2003/0142590 A1 * | 7/2003 | Eschenbrenner | A24F 15/005 368/107 |
| 2004/0001001 A1 * | 1/2004 | Perlman | A24F 47/00 340/573.1 |
| 2004/0031498 A1 * | 2/2004 | Brue | A24F 15/005 131/270 |
| 2004/0201480 A1 * | 10/2004 | Snyder | G09B 23/28 340/573.1 |
| 2005/0053883 A1 * | 3/2005 | Faber | 431/253 |
| 2005/0141346 A1 * | 6/2005 | Rawls | G09B 19/00 368/10 |
| 2006/0180165 A1 * | 8/2006 | Letovsky | A24F 47/00 131/270 |
| 2006/0281037 A1 * | 12/2006 | Faber | 431/253 |
| 2008/0160463 A1 | 7/2008 | Biriki | |
| 2009/0307045 A1 * | 12/2009 | Chakra et al. | 705/9 |
| 2012/0212339 A1 | 8/2012 | Goldblatt | |
| 2012/0214107 A1 | 8/2012 | Al Gharib | |
| 2013/0113977 A1 * | 5/2013 | Yumiki | G02B 7/021 348/333.08 |
| 2013/0345881 A1 * | 12/2013 | Leise | F24F 11/0086 700/276 |
| 2015/0024355 A1 * | 1/2015 | Ghofrani et al. | 434/236 |
| 2015/0208723 A1 * | 7/2015 | Glazer | A24F 47/00 431/6 |
| 2015/0351655 A1 * | 12/2015 | Coleman | A61B 5/0482 600/301 |

* cited by examiner

SYSTEM AND METHOD TO MANAGE SMOKING

CROSS REFERENCE TO RELATED APPLICATION

This application claims the benefit of U.S. Provisional Patent Application No. 61/932,510 filed on Jan. 28, 2014, the entirety of which is incorporated herein by reference.

TECHNICAL FIELD

This disclosure relates to smoking consumption management and, in particular, to a cigarette lighting device that can be programmed to assist smoking reduction, management, and/or elimination.

BACKGROUND

There are many smoking management and cessation solutions on the market. Known smoking cessation devices and products include nicotine gums, nicotine patches, electronic cigarettes, pills, and medications. These devices introduce nicotine or other chemicals into the body of a smoker. Passive treatments such as hypnosis are sometimes utilized in an attempt to reduce or quit smoking. There are also self-reporting systems for smokers to record cigarette consumptions. However, these systems are passive and often require manual recordation. They do not play an active role in preventing the smokers from smoking. Measuring one's smoking habits can help change the person's behavior.

BRIEF DESCRIPTION OF THE DRAWINGS

The present disclosure is illustrated by way of example, and not by way of limitation, in the figures of the accompanying drawings.

DETAILED DESCRIPTION

Embodiments of the present disclosure may include a cigarette lighting device (herein referred to as a "lighter") including a processor configured to record a usage history relating to the lighter (e.g., a history of smoking related usage) over time. Further, the processor of the lighter may be configured to selectively disable the lighter according to a smoking management plan, thus preventing the user from using the lighter to smoke at certain specified times. The smoking management plan may be specified by a user of the lighter or recommended by a smoking management professional such as a doctor. In one embodiment, the processor of the lighter may be configured to disable a heating element of the lighter according to rules or protocols established by the smoking management plan. The heating element can be a spark generator (such as circuitry to generate electric arc) or a flameless heating element (such as an electric heating coil) that may be used to light a cigarette. A cigarette is herein deemed to include any products (including tobacco or non-tobacco product) that are consumed by smoking. By disabling the heating element of the lighter (i.e., disabling the ability to light a cigarette) from activation at specified times according to the rules of the smoking management plan, the amount of cigarette consumption by the user may be managed according to the smoking management plan.

Embodiments of the present disclosure may further include a computing device operatively coupled to the lighter over a communication link. The computing device can be any suitable computer, such as, a smart phone, a portable computer, a tablet, a desktop computer, a computing cloud (e.g., a server in the cloud), or similar devices. The computing device may provide a user interface through which the user may enter one or more target values for the smoking management plan. For example, the user may enter a target number of cigarettes per day he or she plans to smoke that day or after an established period of time. The target number of cigarettes may be smaller than the current daily cigarette consumption (or consumption over a period of time), and the smoking management plan may include a day-to-day cigarette allowance that declines over a specified amount of time until the daily consumption (or consumption over a period of time) of cigarettes reaches a target value.

The user may further use the user interface to issue commands that may cause transmission of the smoking management plan, over the communication link, to a data store in the lighter. The processor in the lighter may execute a smoking management application to selectively disable the heating element of the lighter from activation to enforce the schedule of cigarette consumption according to the smoking management plan.

Embodiments of the present disclosure relate to a lighter including a heating element, a data store to store a smoking management plan including one or more rules, and a processor, operatively coupled to the data store and the heating element, to selectively disable activation of the heating element based on the smoking management plan.

Embodiments of the present disclosure relate to a lighter including a heating element, a data store, and a processor, operatively coupled to the data store and the heating element, to detect an activation of the heating element, determine occurrence of a smoking event based on the activation of the heating element, and record the occurrence of the smoking event in a record stored in the data store.

Embodiments of the present disclosure relate to a method including detecting a request to activate a heating element of a lighter, in response to detecting the request to activate, determining a history of one or more smoking events occurring in a determined period of time, determining whether the history of the one or more smoking events complies with one or more rules of a smoking management plan, in response to determining that the history of the one or more smoking events does not comply with the one or more rules, disabling activation of the heating element, and in response to determining that the history complies with the one or more rules, enabling the activation of the heating element.

Embodiments of the present disclosure relate to a method including detecting an activation of a heating element of a lighter, determining an occurrence of a first smoking event based on the activation of the heating element, and recording the occurrence of the first smoking event in a record.

Figure 1:
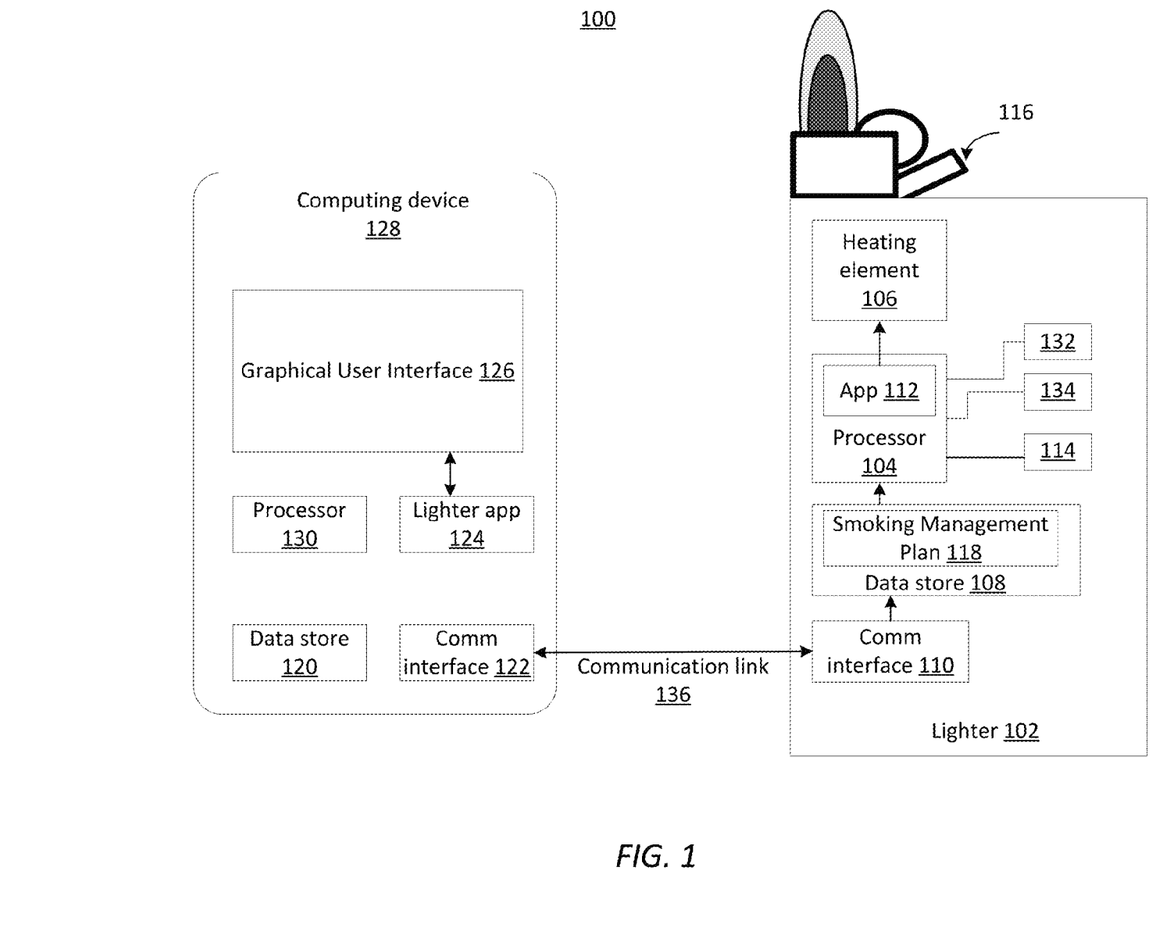
FIG. 1 illustrates a smoking management system according to an embodiment of the present disclosure.

FIG. 1 illustrates a smoking management system 100 according to an embodiment of the present disclosure. As shown in FIG. 1, system 100 may include a lighter 102 and a computing device 128 operatively coupled to the lighter 102 via a communication link 136. In one embodiment, the lighter 102 may further include a processor 104, a heating element 106 (such as a spark generator or a flameless electrical heating coil), a data store 108, a communication interface 110, and a display 114. In addition, the lighter 102 may further include an energy tank (not shown) to store fuel (e.g., pressurized butane) that may be released through a valve (not shown) in the form of a narrow fume stream into the air. Moreover, the lighter 102 may optionally include a clock 132 to provide a current time and date, and a global positioning system 134 to provide a reading of the lighter location. Lighter 102 may further include an ignition trigger (e.g., a lever or a depressible button) 116 that, when pressed, may cause the heating element 106 to start generating a fire source for lighting up a cigarette. For example, the heating element 106 may include a spark generator that may generate sparks (e.g., electric arc) when a user presses the ignition trigger 116. The sparks may light up the narrow fume stream in the air to produce a flame. A sustained flame may be used to light a cigarette.

In one embodiment, processor 104 of the lighter 102 may be any suitable hardware processing device, such as a central processing unit (CPU), a digital signal processor (DSP), an application-specific integrated circuit (ASIC), or a programmable logic controller (PLC), that may be programmed with a smoking management application 112 to record the smoking-related usage of the lighter 102 and/or to disable the heating element 106 of the lighter 102 according to certain rules set forth in a smoking management plan 118. The rules of the smoking management plan 118 include programs or sets of instructions that define limitations, requirements, and protocols relating to the usage of the lighter 102.

The data store 108 may be a memory device, operatively coupled to the processor 104, to store the smoking-related usage of the lighter 102. For example, each time the processor 104 detects a smoking event, the processor 104 may record the occurrence of the cigarette consumption stored in the data store 108. The record may include time and location of the occurrence. Further, the data store 108 may store a smoking management plan 118 that may be received from the computing device 128 via communication link 136 and communication interface 110. Alternatively, the smoking management application 112 executing on processor 104 may calculate the smoking management plan 118 based on certain target values received from the computing device or input by a user to the data store 108.

In one embodiment, the communication link 136 comprises a wired or wireless data communication link according to a suitable standard such as Bluetooth®, a near field communication (NFC) standard, Zigbee®, or any suitable communication protocols. Communication interface 110 may include an antenna, a network card, a USB port, and firmware that may transmit and receive data to and from computing device 128. For example, the smoking management application 112 may pull the smoking management plan 118 or the target values specified by the user from the computing device 128. Alternatively, the computing device 128 may push the smoking management plan 118 or the target values to the lighter 102 that may be stored in the data store 108.

In one embodiment, the display 114 may be operatively coupled to the processor 104 to display information related to the usage of the lighter 102. For example, in one embodiment, the display 114 may include one or more indicator lights to show a status of the lighter 102. For example, a user of lighter 102 may press the trigger 116 from a released position to a first position to check how many indicators can turn on. Each turned-on indicator may indicate a multiple (e.g., one or two) of smoking events that the lighter 102 can still carry out. So, for example, if three out of five indicators are turned on when trigger 116 is at the first position, it means that the user can still use the lighter for six (3×2) times over a specified period of time. If there are still smoking events allowed on the lighter 102, the user may further press the trigger 116 to a second position to activate the heating element 106 to light up a cigarette. But if all of the indicators are off when the user checks, the user may know that the lighter 102 cannot be used for smoking for the time being. Thus, the user of the lighter 102 may learn, before attempting to use the lighter to light a cigarette, whether he or she can use the lighter to smoke a cigarette.

In another embodiment, the display 114 may include colored indicators to display a status of the lighter 102. For example, the colored indicator may have green, yellow, and red colors, with green indicating that the lighter 102 still has smoking events left, yellow indicating that the available smoking events is running low (e.g., less than two), and red indicating that the lighter has run out of smoking events for the time being.

The display 114 may alternatively include a screen (such as a liquid crystal screen (LCD)) to display information relating to cigarette consumption. For example, the display 114 may show how many cigarettes the user has smoked over a period of time (e.g., within a twenty-four hour period of time), how many cigarettes the user can consume over a period of time before the lighter 102 is disabled (e.g., two more cigarettes allowed for the day), and/or how long the heating element 106 is going to be disabled until it is enabled again (e.g., a countdown clock indicating time to enabling of the lighter 102).

In one embodiment, the computing device 128 may work cooperatively with the lighter 102 to provide additional computational resources. The computing device 128 may include a smart phone, a tablet computer, a desktop computer, or a computing cloud (e.g., a server in the cloud). As shown in FIG. 1, the computing device 128 may include a processor 130, a data store 120, and a communication interface 122. The processor 130 may be any suitable hardware processing device, such as a central processing unit (CPU), a digital signal processor (DSP), an application-specific integrated circuit (ASIC), or a programmable logic controller (PLC). The data store 120 may be a memory device, operatively coupled to the processor 130, to store, among others, code and data relating to managing the lighter 102. The communication interface 122 may include an antenna, a network card, a USB port, and firmware that may transmit and receive data to and from the communication interface 110 of the lighter 102. Additionally, the communication interface 122 may provide network connections to connect the computing device 128 to the Internet.

In one embodiment, the computing device 128 may be a portable computing device (such as a smart phone) that operates under a computing environment (e.g., Android™, Windows®, iOS®). Within the computing environment, the processor 130 may be configured to execute a lighter application 124 that may provide additional computation support to the lighter 102. The lighter application 124 may include a graphical user interface (GUI) 126 through which the user may enter certain target values for the smoking management plan 118. Further, the GUI 126 may display performance data (such as progress on cigarette consumption reduction) to the user.

The smoking management system 100 may run under various modes. In one embodiment, the system 100 may run under an assessment mode to measure data relating to a user's smoking habit. Under the assessment mode, the processor 104 may execute the smoking management application 112 to record statistics of the user's cigarette consumption. Under the assessment mode, the lighter 102 is allowed to operate continuously without interruption. For example, the smoking management application 112 may use the clock 132 to record the time of each smoking event and use the GPS 132 to record the location of each smoking event. A smoking event may be defined as one or more activations of the heating element 106 within a pre-determined time period (e.g., 30 seconds) to exclude false alarms such as repeated ignition of the trigger 116 because the flame is extinguished prematurely. The measurements of smoking events may be stored in a data record in the data store 108 and the data record may be transmitted to the computing device 128 when the lighter 102 and the computing device 128 are communicatively coupled (or in sync). At the computing device 128, the processor 130 may execute the lighter application 124 to receive the data record of smoking events by a user and calculate statistics based on the record. For example, the lighter application 124 may compute the average number of cigarettes smoked over a determined period of time (e.g., daily) at a particular location (e.g., at home). In another example, the lighter application 124 may calculate conditional statistics taking into consideration other factors such as, for example, how many cigarettes are smoked during work days and how many cigarettes are smoked during weekends. These statistics may be used to generate the smoking management plan for the user.

In one embodiment, the lighter application 124 may also register the user and create a user account for the user. After the creation of the user account, the user may be associated with a user identifier (user ID) and a password pair to secure the user data. Additionally, the user ID may be associated with all data objects stored in the data store 120 relating to the user so that when the data objects are transmitted to the lighter 102, the processor 104 of the lighter 102 may associate the data objects with the user. In one embodiment, the lighter application 124 may additionally receive personal information from the user via the GUI 126. For example, the user may enter information such as, for example, the user's gender, age, weight, how long he or she has been smoking, the brand of cigarette he or she prefers to smoke, and health information via the GUI 126. The user information may be used to form a user smoking profile. The lighter application 124 may also take into account the user smoking profile when calculating the smoking management plan. In one embodiment, with the user ID, a single person may use two lighters and his or her data will be stored under a single user ID. In another embodiment, one lighter may be used by two people, each with their own unique user ID.

In one embodiment, the lighter application 124 may also receive one or more targets either via the GUI 126 from the user or by retrieving pre-set targets (e.g., from a database via the Internet). The targets may be selected by matching the user smoking profile with smoking management plans for known smoker profiles. The targets can be in the form of cigarette consumption reduction over a specific period of time (e.g., reducing the cigarette consumption by 20% over six months) or a limit on how many cigarettes the user may smoke for a given time period (e.g., one cigarette per two hours).

In one embodiment, the system 100 may run under a smoking management mode. Under this smoking management mode, the lighter application 124 may calculate a smoking management plan 118 based on the target values, the user smoking profile, and/or the statistics of the current cigarette consumption. The smoking management plan 118 may include rules that, when violated, cause the processor 104 to disable the heating element 106 from activation, thus preventing the user from using the lighter 102 to light a cigarette. In one embodiment, the smoking management plan 118 may include how many cigarettes the user may smoke for each day over a time period defined by the smoking management plan 118 or the rate of cigarette smoking. For example, the smoking management plan 118 may include requirements that call for smoking no more than N cigarettes (a number greater than or equal to one) a day and one cigarette every M (another number greater than or equal to one) hours or minutes. Therefore, whenever a smoking event occurs, the smoking management plan 118 calls for disabling the heating element 106 of the lighter 102 for M minutes before enabling it again, and when the user uses up the N cigarette allowance for the day, the smoking management plan calls for disabling the heating element 106 for the day. The calculated smoking management plan 118 may provide for decreasing N over the specified period of time (e.g., 3 months) until the user reaches the target level of cigarette consumption.

In another embodiment, the smoking management plan 118 may provide for the total number of cigarettes the user may smoke for each day over the time period defined by the plan. Therefore, the smoking management plan 118 may call for disabling the heating element 106 for the day if the count of smoking events reaches the total number allowed for the day. The lighter 102 may be enabled after the day (e.g., 24 hours) is over.

In one embodiment, instead of calculating the smoking management plan 118, a user may manually set or customize a smoking management plan via the GUI 126. The user may set rules of the smoking management plan as the user feels comfortable. In one embodiment, pre-set smoking management plans may be used. These pre-set smoking management plans may have been designed by medical professionals for various smoking profiles. Therefore, a pre-set smoking management plan may be selected based on the user's smoking profile.

In one embodiment, the smoking management plan may be transmitted from the computing device 128 to the lighter 102. For example, GUI 126 may display icons associated with a smoking management plan 118 and the lighter 102. By dragging the icon of the smoking management plan 118 to the icon of the lighter 102, the computing device 128 may push a data object including the smoking management plan to the data store 108 of the lighter 102 via the communication interfaces 122, 110 and the communication link 136.

In another embodiment, instead of the computing device 128, the processor 104 of the lighter 102 may calculate the smoking management plan 118 for the user. The processor 104 may receive target values and a user smoking profile from the computing device 128 via the communication link 122 and calculate the smoking management plan 118 based on the target values, user smoking profile, and the current smoking statistics already recorded in the data store 108.

Once a smoking management plan 118 is stored in the data store 108, the smoking management application 112 executing on the processor 104 may selectively disable the heating element 106 from activation base on a comparison of the smoking history for a period of time (e.g., a day) with the rules specified in the smoking management plan. In one embodiment, the smoking management application 112 may include a smoking event counter and a timer. Each time, the smoking management application 112 detects a smoking event (e.g., a spark generator successfully generates sparks to light up a flame within a specific period of time (e.g., 30 seconds)), it may increase the count of the smoking event counter for the day. In an example, if the count of the smoking events for the day exceeds the allowed cigarette consumption for the day, the smoking management application 112 may cause the disablement of the heating element 106. The smoking management application 112 may also send a notification to the user. Similarly, if the smoking management plan 118 includes a requirement to disable the lighter 102 for a down time (e.g., two hours), in response to detecting a smoking event, the smoking management application 112 may disable the heating element 106 from activation and start the timer to count down the down time. When the timer reaches the end of the down time period, the smoking management application 112 may enable the heating element 106 again.

Figure 2A:
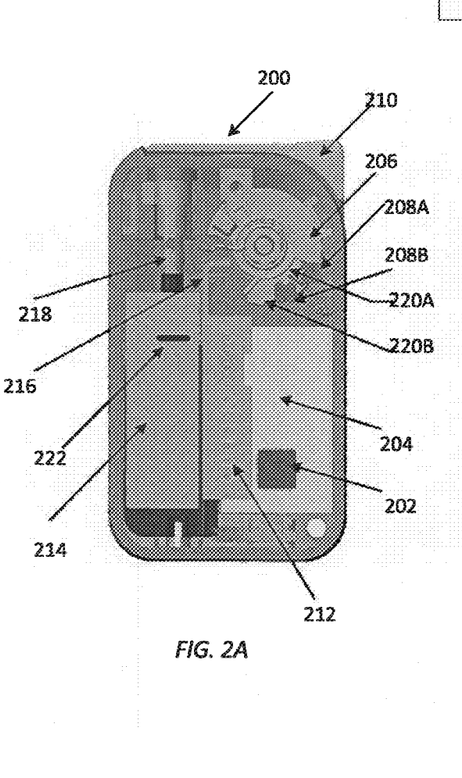
FIGS. 2A-2C illustrate cross-sections of a lighter including a spark generator in operation according to an embodiment of the present disclosure.
Figure 2B:
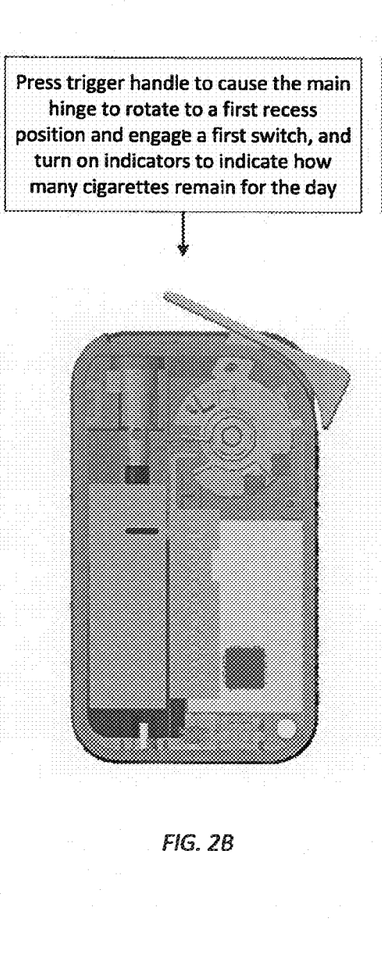
Figure 2C:
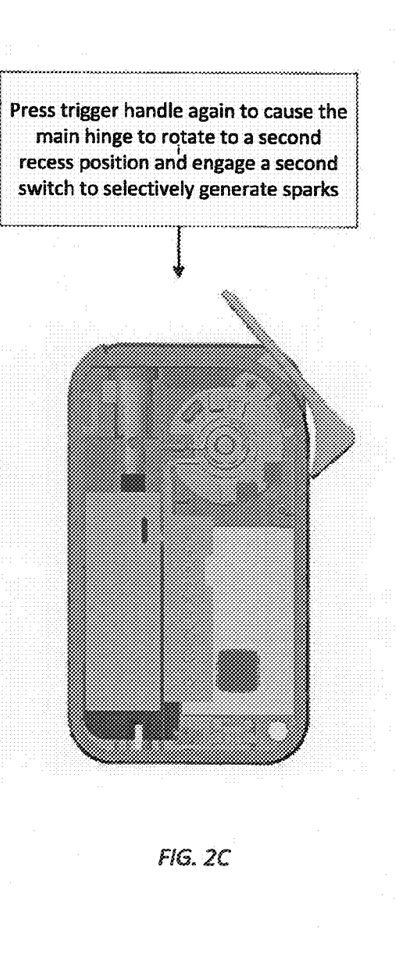

In one embodiment, the lighter 102 may be disabled by disabling the heating element 106 of a spark generator. The spark generator may include a piezoelectric ignition system that may generate an electric arc to light up the narrow stream of fuel released in the air. FIGS. 2A-2C show cross-sections of a lighter including a spark generator in operation according to an embodiment of the present disclosure. As shown in FIG. 2A, a lighter 200 may include a processor 202 operatively coupled to a control circuit 204. The control circuit 204 may further include a first switch 208A and a second switch 208B, and suitable circuitries to generate an electric arc (or sparks) and control the operations of the lighter 200 according to instructions executed on the processor 202. The lighter 200 may also include a hinge 206 that may further include a first recess 220A and a second recess 220B. In one embodiment, the first switch 208A is situated in the first recess 220A and the second switch 208B is situated in the second recess 220B of the hinge 206 so that a rotation of the hinge 206 can engage the first switch 208A through the recess 220A and a further rotation of the hinge 206 may disengage the first switch 208A and engage the second switch 208B through the second recess 220B.

The lighter 200 may further include a trigger handle 210 coupled to the hinge 206. In one embodiment, the trigger 210 may be pushed from an OFF position to a first activated position as shown in FIG. 2B, and then pushed from the first activated position to a second activated position as shown in FIG. 2C. At the first activated position, the trigger 210 may push the hinge 206 to rotate to a first position at which the first recess 220A forces the first switch 208A to engage while the second switch 208B is disengaged as shown in FIG. 2B. At the second activated position, the trigger 210 may push the hinge 206 to further rotate to a second position at which the second recess 220B forces the second switch 208B to engage while the first switch 208A is disengaged as shown in FIG. 2C.

In one embodiment, the lighter 200 may further include one or more indicators 212 operatively coupled to the control circuit 204. Each indicator may be individually turned on and off under the control of the processor 202 based on how many cigarettes a user can smoke under his or her smoking management plan and how many he or she has consumed. For example, when the trigger 210 is pushed to the first activated position, zero or more indicators may be turned on under the instruction of the processor 202 according to the smoking management plan and the number of cigarettes that has been smoked by the user. Each ON indicator may indicate a fixed number (e.g., two) of cigarettes that are still available for the user to smoke. If all indicators are OFF, the user knows that the cigarette consumption for a time period (e.g., a day) has exceeded the number allowed by the smoking management plan, thus warning the user not to operate the lighter 200.

In one embodiment, the lighter 200 may also include a fuel tank 214, a release channel 218 coupled to the tank 214, a valve 222, and a lever 216. The fuel tank 214 stores a fuel (e.g., pressurized butane) that may be released through an opened valve 222 and the release channel 218 in the form of a narrow fume stream into the air. The lever 216 is coupled between the hinge 206 and the valve 222 so that the rotation of the hinge 206 may control the open and close of the valve 222. In one embodiment, the valve 222 is commonly at the closed position so that the fuel stored in the fuel tank 214 is not released to the air. But, when the hinge 206 is pushed to the second activated position, the hinge 206 may be engaged with the lever 216 to pull the lever 216 as shown in FIG. 2C. The pulled lever 216 may cause the valve 222 to move to an opened position, thus releasing a stream of fuel through the release channel 218 into the air.

In one embodiment, a user may push the trigger 210 through the first and second activated positions despite that the indicators 212 show there is no cigarette to smoke. When this happens, the hinge 206 is pushed to the second activated position as shown in FIG. 2C and the second switch 208A is engaged by the hinge 206. In response to receiving an electrical signal that the second switch 208B is engaged, the processor 202 may determine whether the user is allowed to smoke based on the number of cigarettes he or she has consumed during a pre-determined period of time (e.g., a day) and other applicable rules of the smoking management plan. If the user can smoke, the processor 202 may allow certain electrical devices (such as a transformer) on the control circuit 204 to engage and generate a high voltage to cause a spark (e.g., an electric arc). The generated arc may light up the fuel in the air to produce a flame to light up a cigarette. But, if the user cannot smoke at a given time according to the smoking management plan, the processor 202 may disable activation of the spark generation circuit, thus preventing the ignition of the fuel and preventing the user from lighting a cigarette with the lighter.

In one embodiment, when the user releases the trigger 210 from either the first activated position (as shown in FIG. 2B) or from the second activated position (as shown in FIG. 2C), the trigger 210 automatically resets by a spring (not shown) to its OFF position as shown in FIG. 2A. In the OFF position, the valve 222 may be closed again and thus extinguish any flame.

In one embodiment, the processor 202 may record the occurrences of smoking events either under the assessment mode or the management mode. A smoking event may be defined as one or more activation of the lighter 200 within a small time window (e.g., 30 seconds). The time window is used to exclude false alarms such as the flame is blown out by wind and the user needs to reignite the lighter 200. Under the assessment mode, the processor 202 may allow the user to use the lighter 200 without disabling the spark generation, but the processor 202 records information (such as time, locations) of each smoking events in a memory (not shown). Under the management mode, the processor 202 may record a usage history of cigarette consumption and compare the usage history with rules of the smoking management stored in the memory. The processor 202 may cause the control circuit 204 to disable the spark generation circuit if the cigarette usage history violates the rules of the smoking management plan.

In one embodiment, the data of cigarette consumption stored in the memory may be transmitted to a computing device (e.g., the computing device 128 as shown in FIG. 1). The computing device 128 may provide a lighter application 124 to analyze, provide visualization, display, and publish the data to the user.

Figure 3A:
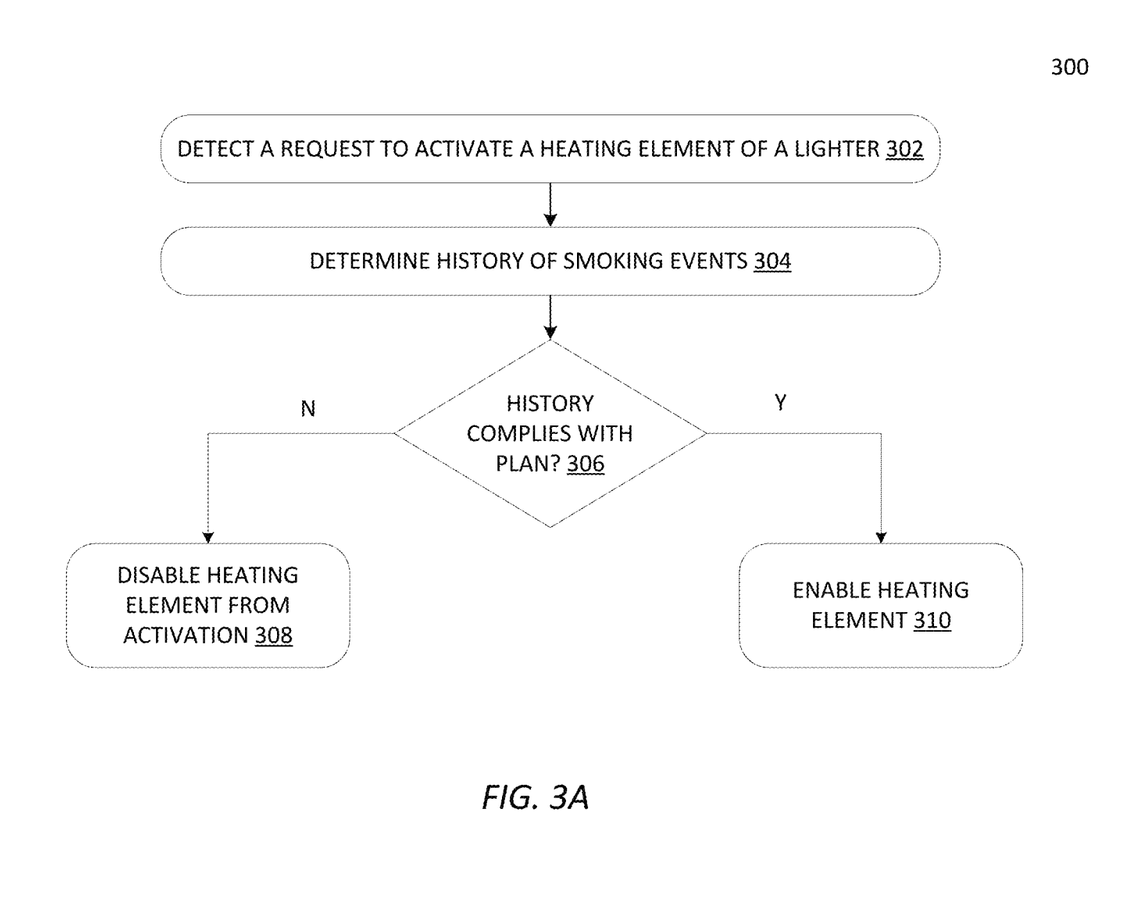
FIG. 3A is a flow diagram illustrating a method to manage smoking using a lighter according to an embodiment of the present disclosure.

FIG. 3A is a flow diagram illustrating a method 300 to manage smoking using the lighter 102 (or 200) according to an embodiment of the present disclosure. The method 300 may be performed by processing logic that comprises hardware (e.g., circuitry, dedicated logic, programmable logic, microcode, etc.), software (e.g., instructions run on a processing device to perform hardware simulation), or a combination thereof.

For simplicity of explanation, methods are depicted and described as a series of acts. However, acts in accordance with this disclosure can occur in various orders and/or concurrently, and with other acts not presented and described herein. Furthermore, not all illustrated acts may be required to implement the methods in accordance with the disclosed subject matter. In addition, the methods could alternatively be represented as a series of interrelated states via a state diagram or events. Additionally, it should be appreciated that the methods disclosed in this specification are capable of being stored on an article of manufacture to facilitate transporting and transferring such methods to computing devices. The term article of manufacture, as used herein, is intended to encompass a computer program accessible from any computer-readable device or storage media. In one implementation, the methods may be performed by the smoking management application executed on the processor 104 as shown in FIG. 1 or processor 202 as shown in FIG. 2A.

Referring to FIG. 3A, at 302, the processing logic may detect a request to activate a heating element of the lighter. The request may be generated by a user of the lighter pushing a trigger of the lighter in an attempt to ignite the heating element to light up a cigarette.

At 304, in response to detecting the request to activate the heating element, the processing logic may execute a smoking management application to determine a history of smoking events that have occurred over a specified period of time (e.g., in a day of twenty four hours). The history may include a count of smoking events, time of smoking events and/or locations at which the smoking events occur. The processing logic may make the determination based on a record of smoking events stored in a data store.

At 306, the processing logic may determine whether the history of smoking events complies with one or more rules set forth in a smoking management plan. The smoking management plan may have been calculated or determined for the user and stored in a data store (e.g., a memory). The processing logic may retrieve the smoking management plan from the data store. The smoking management plan may include one or more rules that specify how the user may smoke. For example, a rule may specify how many cigarettes that the user may smoke in a day. When his count of cigarettes reaches the limit, the user is in violation of this rule.

At 308, in response to determining that the history of smoking events does not comply with any rule of the smoking management plan, the processing logic may disable activation of the heating element (e.g., preventing a spark generator or an electrical heating coil from activation), thus preventing the user from using the lighter to light a cigarette.

At 310, in response to determining that the history of smoking events complies with the one or more rules of the smoking management plan (i.e., the user is still allowed to smoke according to the plan), the processing logic may enable the heating element to allow the user to light up a cigarette. After the ignition of the lighter to light a cigarette, the processing logic may record the occurrence of the smoking event in the smoking record of the user in the data store.

Figure 3B:
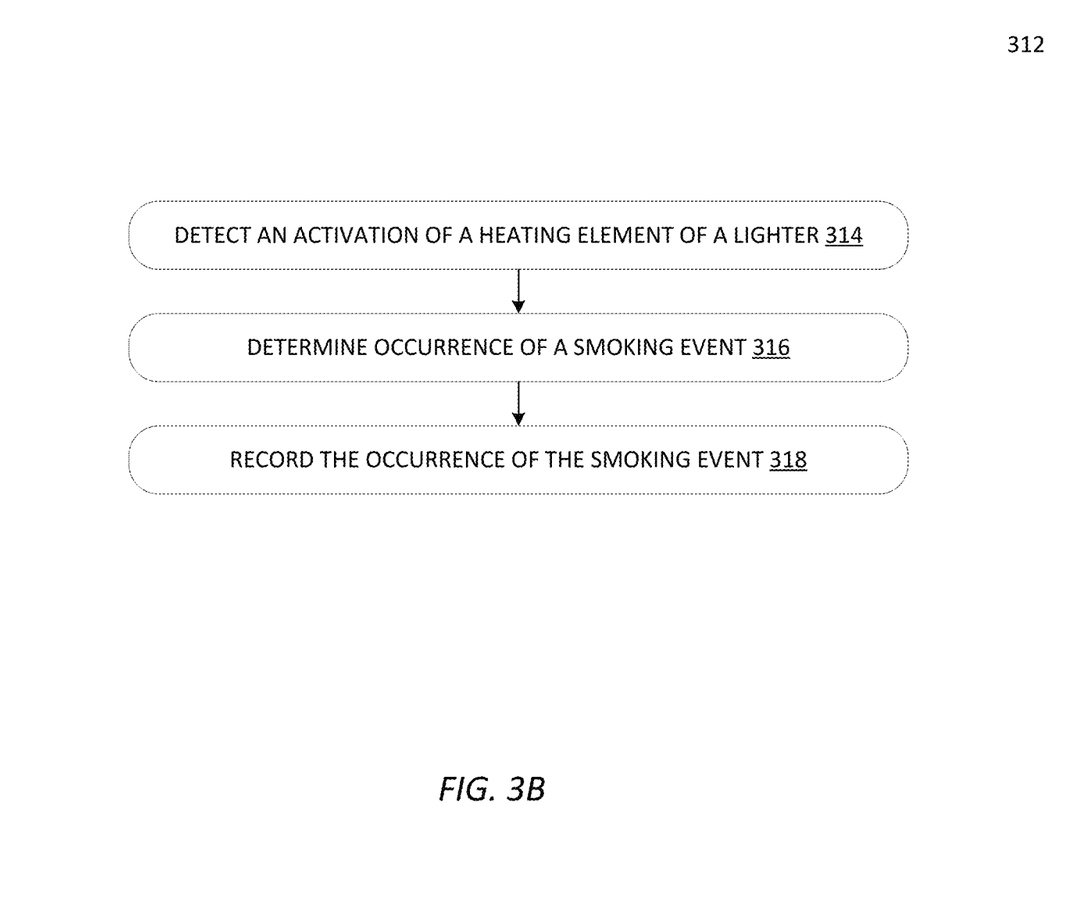
FIG. 3B is a flow diagram illustrating a method to assess the smoking habit of a user according to an embodiment of the present disclosure.

FIG. 3B is a flow diagram illustrating a method 312 to assess the smoking habit of a user according to an embodiment of the present disclosure. The method 312 may be performed by processing logic that comprises hardware (e.g., circuitry, dedicated logic, programmable logic, microcode, etc.), software (e.g., instructions run on a processing device to perform hardware simulation), or a combination thereof.

For simplicity of explanation, methods are depicted and described as a series of acts. However, acts in accordance with this disclosure can occur in various orders and/or concurrently, and with other acts not presented and described herein. Furthermore, not all illustrated acts may be required to implement the methods in accordance with the disclosed subject matter. In addition, the methods could alternatively be represented as a series of interrelated states via a state diagram or events. Additionally, it should be appreciated that the methods disclosed in this specification are capable of being stored on an article of manufacture to facilitate transporting and transferring such methods to computing devices. The term article of manufacture, as used herein, is intended to encompass a computer program accessible from any computer-readable device or storage media. In one implementation, the methods may be performed by the smoking management application executed on the processor 104 as shown in FIG. 1 or processor 202 as shown in FIG. 2A.

Referring to FIG. 3B, at 314, the processing logic may detect an activation of a heating element of lighter. At 316, the processing logic may determine whether a smoking event has occurred based on the activation of the heating element. The processing logic may determine the occurrence of a smoking event based on certain characteristics of the activation of the heating element. For example, the processing logic may determine that a smoking event occurred if the heating element is activated longer than a pre-determined time (e.g., three seconds). At 318, in response to determining that a smoking event has occurred, the processing logic may record the occurrence in a smoking record stored in a data store. The record may include the timing and location of the smoking event. Subsequently, the processing logic may transmit the record to a computing device via a data communication link. The computing device may include a lighter application and GUI to present the smoking data to the user.

In one embodiment, the user may further upload the smoking record to the Internet. For example, the user may upload the smoking record to his healthcare provider (e.g., his doctor, nurse, insurer, employer or any other relevant entities) or to a social media site (e.g., his Facebook page) to share with others.

Figure 4:
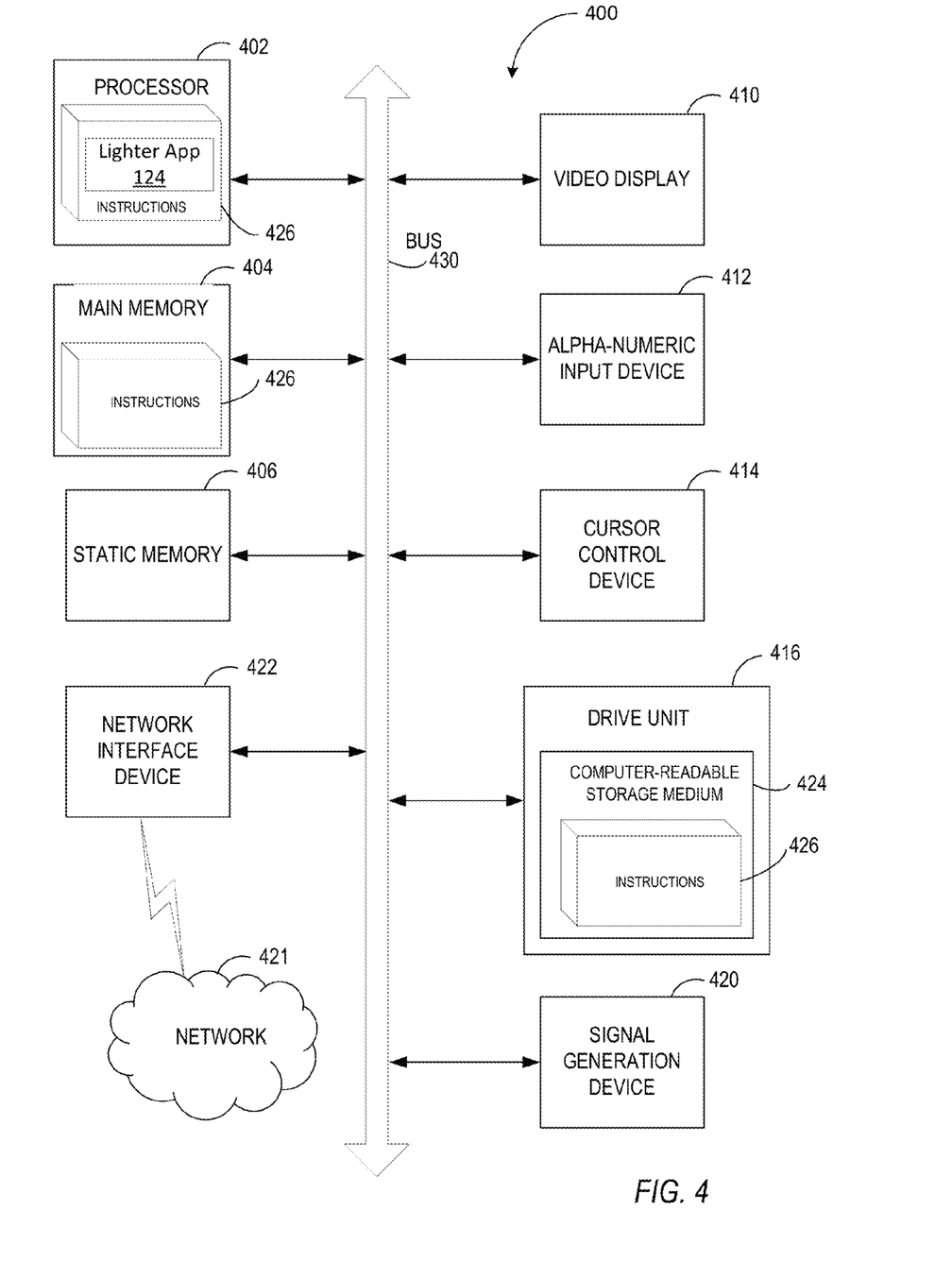
FIG. 4 is a block diagram illustrating an exemplary computer system, according to an embodiment of the present disclosure.

FIG. 4 illustrates a diagrammatic representation of a machine in the exemplary form of a computer system 400 within which a set of instructions for causing the machine to perform any one or more of the methodologies discussed herein may be executed. In alternative implementations, the machine may be connected (e.g., networked) to other machines in a LAN, an intranet, an extranet, or the Internet. The machine may operate in the capacity of a server or a client machine in a client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The exemplary computer system 400 includes a processing device (processor) 402, a main memory 404 (e.g., read-only memory (ROM), flash memory, dynamic random access memory (DRAM) such as synchronous DRAM (SDRAM) or Rambus DRAM (RDRAM), etc.), a static memory 406 (e.g., flash memory, static random access memory (SRAM), etc.), and a data storage device 416, which communicate with each other via a bus 430.

Processor 402 represents one or more general-purpose processing devices such as a microprocessor, central processing unit, or the like. More particularly, the processor 402 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processor 402 may also be one or more special-purpose processing devices such as an application specific integrated circuit (ASIC), a field programmable gate array (FPGA), a digital signal processor (DSP), network processor, or the like. The processor 402 is configured to execute instructions 426 for performing the operations and steps discussed herein. The instructions 426 may include the lighter application 124 as shown in FIG. 1.

The computer system 400 may further include a network interface device 422. The computer system 400 also may include a video display unit 410 (e.g., a liquid crystal display (LCD), a cathode ray tube (CRT), or a touch screen), an alphanumeric input device 412 (e.g., a keyboard), a cursor control device 414 (e.g., a mouse), and a signal generation device 420 (e.g., a speaker).

The data storage device 416 may include a computer-readable storage medium 424 on which is stored one or more sets of instructions 426 (e.g., software) embodying any one or more of the methodologies or functions described herein. The instructions 426 may also reside, completely or at least partially, within the main memory 404 and/or within the processor 402 during execution thereof by the computer system 400, the main memory 404 and the processor 402 also constituting computer-readable storage media. The instructions 426 may further be transmitted or received over a network 421 via the network interface device 422.

While the computer-readable storage medium 424 is shown in an exemplary implementation to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

In the foregoing description, numerous details are set forth. It will be apparent, however, to one of ordinary skill in the art having the benefit of this disclosure, that the present disclosure may be practiced without these specific details. In some instances, well-known structures and devices are shown in block diagram form, rather than in detail, in order to avoid obscuring the present disclosure.

Some portions of the detailed description have been presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "segmenting", "analyzing", "determining", "enabling", "identifying," "modifying" or the like, refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices.

The disclosure also relates to an apparatus for performing the operations herein. This apparatus may be specially constructed for the required purposes, or it may include a general purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions.

The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an embodiment" or "one embodiment" or "an implementation" or "one implementation" throughout is not intended to mean the same embodiment or implementation unless described as such.

Reference throughout this specification to "one embodiment" or "an embodiment" means that a particular feature, structure, or characteristic described in connection with the embodiment is included in at least one embodiment. Thus, the appearances of the phrase "in one embodiment" or "in an embodiment" in various places throughout this specification are not necessarily all referring to the same embodiment. In addition, the term "or" is intended to mean an inclusive "or" rather than an exclusive "or."

It is to be understood that the above description is intended to be illustrative, and not restrictive. Many other implementations will be apparent to those of skill in the art upon reading and understanding the above description. The scope of the disclosure should, therefore, be determined with reference to the appended claims, along with the full scope of equivalents to which such claims are entitled.

What is claimed is:

1. A lighter comprising:
    a heating element that, when activated, is used to light up a smoking product;
    a data store to store a smoking management plan comprising one or more rules; and
    a processor, operatively coupled to the data store and the heating element, to disable activation of the heating element based on the one or more rules of the smoking management plan, wherein disabling the activation of the heating element prevents using the heating element to light up the smoking product, and wherein the disabling the activation of the heating element cannot be manually overridden prior to complying with the one or more rules.

2. The lighter of claim 1, wherein the heating element comprises a spark generator, and wherein the processor is to disable activation of the spark generator based on the one or more rules set forth in the smoking management plan, and wherein disabling the activation of the spark generator prevents using the spark generator to light up the smoking product.

3. The lighter of claim 1, wherein the heating element comprises a flameless heating element, and wherein the processor is to disable activation of the flameless heating element based on the one or more rules set forth in the smoking management plan, and wherein disabling the activation of the flameless heating element prevents using the flameless heating element to light up the smoking product.

4. The lighter of claim 3, wherein the flameless heating element comprises a heating coil.

5. The lighter of claim 1, further comprising:
    a communication interface configured to couple to a computing device over a communication link, wherein the processor is further configured to receive the smoking management plan from the computing device via the communication interface.

6. The lighter of claim 5, wherein the computing device comprises a smart phone, and wherein the communication link is a wireless data communication link between the smart phone and the communication interface of the lighter.

7. The lighter of claim 5, wherein the computing device comprises a second processor to:
    receive one or more target values of cigarette consumption from a user interface, and
    generate the one or more rules of the smoking management plan based on the one or more target values.

8. The lighter of claim 1, wherein the processor is further configured to, prior to disabling the activation of the heating element:
    determine an occurrence of a smoking event based on an activation of the heating element; and
    increment a count of smoking events occurring in a pre-determined period of time.

9. The lighter of claim 8, further comprising:
    an indicator;
    a control circuit comprising a spark generator circuit, a first switch, and a second switch for operating the lighter; and
    a trigger operatively coupled to the first switch and the second switch, wherein the processor is further configured to:
        in response to detecting that the trigger is pressed to a first position to engage the first switch, cause to display a status of the lighter on the indicator;
        in response to detecting that the trigger is pressed to a second position to engage the second switch, determine whether the activation of the heating element is to be disabled based on the count of the smoking events and the one or more rules; and
        in response to determining that the activation of the heating element is to be disabled, cause to disable the spark generator circuit to prevent the heating element from being activated.

10. The lighter of claim 9, wherein the status of the lighter comprise at least one of the count of smoking events occurring in a pre-determined period of time, a number of cigarettes that a user is allowed to smoke over the pre-determined period of time, an indication of whether the user used up a cigarette ration for the pre-determined period of time, or a time that the lighter is to be activated again from a disabled state.

11. The lighter of claim 1, wherein the one or more rules of the smoking management plan comprise at least one of:
    a maximum number of cigarettes that a user is allowed to smoke over a first pre-determined period of time, or
    a second pre-determined time that the user is prohibited from smoking after detecting, by the processor, occurrence of a smoking event.

12. A lighter comprising:
    a fuel tank containing a fuel;
    a control circuit comprising a spark generator circuit, a first switch, and a second switch for operating the lighter;
    a trigger operatively coupled to the first switch and the second switch;
    a data store to store a smoking management plan comprising one or more rules; and
    a processor, operatively coupled to the data store and the control circuit, to:
        in response to detecting that the trigger is pressed to a first position to engage the first switch, cause to display a status of the lighter on an indicator of the lighter;
        in response to detecting that the trigger is pressed to a second position to engage the second switch, determine whether activation of the spark generator circuit is to be disabled based on the status of the lighter and the one or more rules; and
        in response to determining that the activation of the spark generator circuit is allowable,
            cause to release a portion of the fuel;
            cause the spark generator circuit to produce a spark to light up the portion of the fuel; and
            record occurrence of a smoking event in a record stored in the data store;
        and
        in response to determining that the activation of the spark generator circuit is not allowable,
            disable the activation of the spark generator circuit; and
            prevent a manual override of the disabling the activation of the spark generator circuit prior to complying with the one or more rules.

13. The lighter of claim 12, further comprising:
a communication interface coupled to a computing device over a communication link, wherein the processor is further configured to transmit the record to the computing device via the communication interface.

14. The lighter of claim 13, further comprising:
a clock; and
a global positioning system (GPS), wherein the processor is further configured to record, in the record, at least one of a time of the occurrence of the smoking event based on a reading of the clock or a location of the occurrence of the smoking event based on the GPS.

15. The lighter of claim 14, wherein the computing device comprises:
a display; and
a second processor to provide, on the display, a visualization of the record of the occurrence of the smoking event.

16. The lighter of claim 15, wherein the second processor is further to:
receive one or more target values of cigarette consumption via a user interface, and
generate the one or more rules of the smoking management plan in view of the one or more target values and the record.

17. A method comprising:
detecting, by a processor, a request to activate a heating element of a lighter that, when activated, is used to light up a smoking product;
in response to detecting the request to activate, determining a history of one or more smoking events occurring in a period of time;
determining whether the history of the one or more smoking events complies with one or more rules of a smoking management plan;
in response to determining that the history of the one or more smoking events does not comply with the one or more rules, disabling activation of the heating element, wherein disabling the activation of the heating element prevents using the heating element to light up the smoking product, and wherein disabling the activation of the heating element cannot be manually overridden prior to complying with the one or more rules; and
in response to determining that the history of the one or more smoking events complies with the one or more rules, enabling the activation of the heating element.

18. The method of claim 17, wherein the heating element comprises one of a spark generator or a flameless heating element.

19. The method of claim 17, further comprising:
in response to enabling the heating element, determining an occurrence of a smoking event; and
recording the occurrence of the smoking event in the record.

20. The method of claim 17, wherein the history of the one or more smoking events comprises at least one of a count of the one or more smoking events or a location at which the one or more smoking events occur.

21. A method comprising:
detecting, by a processor operatively coupled to a control circuit comprising a spark generator circuit, a first switch, and a second switch of a lighter, that the first switch is engaged;
presenting, by the processor, a status of the lighter on an indicator of the lighter;
detecting, by the processor, that the second switch is engaged, determining whether activation of the spark generator circuit is to be disabled based on the status of the lighter and one or more rules of a smoking management plan;
in response to determining that the activation of the spark generator circuit is allowable,
  causing to release a portion of fuel stored in a fuel tank of the lighter;
  causing the spark generator circuit to produce a spark to light up the portion of the fuel; and
  recording, by the processor, occurrence of a first smoking event in a record; and
in response to determining that the activation of the spark generator circuit is not allowable,
  disabling the activation of the spark generator circuit; and
  preventing a manual override of the disabling the activation of the spark generator circuit prior to complying with the one or more rules.

22. The method of claim 21, further comprising:
transmitting, via a communication interface, the record to a computing device over the communication interface.

23. The method of claim 21, further comprising:
in response to determining that the activation of the spark generator circuit is to be disabled, disabling the activation of the spark generator circuit.

* * * * *